United States Patent [19]

Takahashi

[11] Patent Number: 4,867,137

[45] Date of Patent: Sep. 19, 1989

[54] ELECTRONIC ENDOSCOPE

[75] Inventor: Yutaka Takahashi, Hachioji, Japan

[73] Assignee: Olympus Optical Co., Ltd., Japan

[21] Appl. No.: 168,189

[22] Filed: Mar. 15, 1988

[30] Foreign Application Priority Data

Mar. 19, 1987 [JP] Japan .................................. 62-65303
Jul. 24, 1987 [JP] Japan ................................. 62-185160

[51] Int. Cl.⁴ .............................................. A61B 1/00
[52] U.S. Cl. ........................................... 128/6; 128/4; 358/98
[58] Field of Search .......................... 358/98; 128/6, 4; 333/33

[56] References Cited

U.S. PATENT DOCUMENTS

| | | | |
|---|---|---|---|
| Re. 31,289 | 6/1983 | Moore et al. ........................... 128/6 |
| 4,491,865 | 1/1985 | Danna et al. .......................... 358/98 |
| 4,539,586 | 9/1985 | Danna et al. .......................... 358/98 |
| 4,667,230 | 3/1987 | Arakawa et al. ...................... 358/98 |
| 4,745,471 | 5/1988 | Takamura et al. .................... 358/98 |
| 4,759,346 | 7/1988 | Nakajima ................................ 128/6 |
| 4,766,489 | 8/1988 | Kato ....................................... 358/98 |

Primary Examiner—Leo P. Picard
Assistant Examiner—Jessica Harrison
Attorney, Agent, or Firm—Ostrolenk, Faber, Gerb & Soffen

[57] ABSTRACT

An electronic endoscope includes a solid-state image sensor disposed within the distal end of insertable portion thereof, a picture image processor disposed remote from the solid-state image sensor and a drive circuit for the solid-state image sensor. The electronic endoscope further includes a terminal resistor for impedance matching on input and/or output terminals of the solid-state image sensor within the distal end of the insertable portion thereof, so as to stabilize a signal associated with the solid-state image sensor and obtain a good picture.

6 Claims, 3 Drawing Sheets

ELECTRONIC ENDOSCOPE

BACKGROUND OF THE INVENTION

The present invention relates to an electronic endoscope provided with a solid-state image sensor disposed at the distal end thereof.

Recently, there have been provided electronic endoscopes called as an electronic scope with a solid-state image sensor such as a CCD(charge coupled device) disposed at the distal end thereof for picking up an image of a portion being observed and displaying the image on a screen of a monitor television. These electronic endoscopes have a picture processor and a drive circuit of a solid-state image sensor which are disposed at a position several meters away from the solid-state image sensor. In this structure, a drive signal to be applied to the solid-state image sensor from the drive circuit fails to obtain an accurate representation of a signal waveform at the input terminal of the image sensor because of a long signal transmitting line, so that a good picture can not be obtained. To eliminate this disadvantage, the applicant of the present invention has proposed a solution in Japanese Application Sho No. 60-225368. This application discloses that a plurality of impedance matching circuits composed of a resistor and a capacitor are provided within a light source unit including a drive circuit and the like and one of the plurality of matching circuits is selected according to an electronic endoscope in use so that a drive signal can be an accurate and optimum waveform at an input terminal of the solid-state image sensor.

In addition, another Japanese Laid Open Application Sho No. 60-250608 discloses an electronic endoscope in which circuit parts required to properly operate a solid-state image sensor disposed at the distal end thereof are arranged in the middle of the insertable portion thereof by providing a second hard portion.

In the former application Sho No. 60-225368, a drive signal may or may not obtain an optimum waveform at an input terminal of a solid-state image sensor because of a long signal transmitting line. As a result, in electronic endoscopes with the same cable length, when some of them are combined with a light source unit an accurate square waveform may be produced, whereas when others are combined with the light source unit overshooting, for example, may be caused, thus operations of electronic endosoopes are disadvantageously unstable. In the latter laid-open application Sho No. 61-250608, since the second hard portion is disposed in the middle of the insertable portion of an electronic endoscope, when an electronic endoscope is for use in medical treatment, for example, it greatly inflicts pain upon a patient when the endoscope is inserted into his coelom.

SUMMARY OF THE INVENTION

It is an object of the present invention to provide an electronic endoscope which gives an accurate and stable representation of signal waveform to signals associated with a solid-state image sensor without enlarging the distal end thereof to enable obtaining a good image picture.

The present invention is to dispose a terminal resistor within the distal end of the insertable portion of an endoscope by a solid-state image sensor so as to obtain impedance matching.

According to the present invention, both of a terminal resistor and a solid-state image sensor are disposed within the distal end of an electronic endoscope, so that no distortion in signal waveform may be caused as by reflection of a signal to enable obtaining a good image picture.

DETAILED DESCRIPTION OF THE PREFERRED EMBODIMENTS

Figure 1:
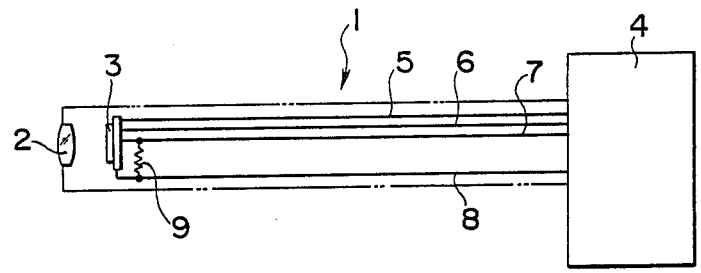
FIG. 1 is schematic diagram illustrating a first embodiment of an electronic endoscope according to the present invention.

In FIG. 1, an electronic endoscope 1 includes an objective lens 2 and a solid-state image sensor 3 provided at the distal end thereof. The proximal end of the endoscope 1 is connected through a connector to a power source unit 4. A power line 5, an image signal output line 6, a drive signal line 7 (though a plurality of lines are practically employed, only one line is shown in FIG. 1) and a grounding line 8 are connected between the power source unit 4 and the image sensor 3. In addition, a terminal resistor 9 is connected to the drive signal line 7 at the distal end of the endoscope 1.

Figure 2:
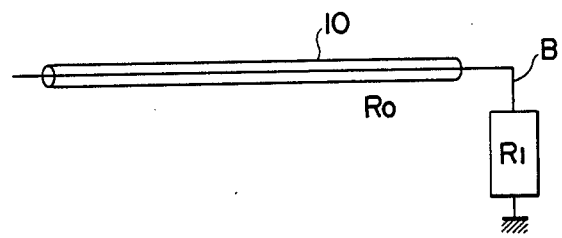
FIGS. 2 and 3 are diagrams explaining the operational concept of the first embodiment.
Figure 3:
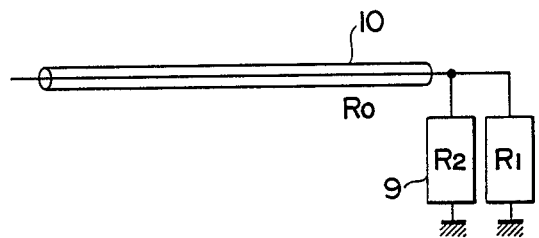

FIGS. 2 and 3 are explanatory diagrams of the operational concept of the present invention. When a signal of square wave form is applied to a cable 10 having a characteristic impedanoe Ro which is connected to a load of an impedance R1 at one end of the cable 10, the signal may generally be reflected at a point B joining the cable 10 and the load to cause non-square wave and phenomena such as overshooting. However, supposing Ro$\approx$R1, namely, both impedances are approximately equal, no reflection occurs.

Considering that the cable 10 and the load correspond to the drive signal line 7 and the image sensor 3 shown in FIG. 1 respectively, the characteristic impedance of the drive signal line 7 is several 10$\Omega$ and the input impedance of the image sensor 3 is more than several K$\Omega$ in practice, thus the impedances of the conductor 7 and image sensor 3 being not matched. As a result, a waveform at the input terminal of the image sensor 3 (which terminal corresponds to the point B in FIG. 2 ) may be distorted. Accordingly, as shown in FIG. 3, when a terminal resistor 9 of impedance R2 is connected in parallel with the image sensor 3 to the input terminal of the latter so as to be Ro$\approx$R1 the impedance matching is established and a waveform of a drive signal at the input terminal of the image sensor 3 will not be distorted. Since the input impedance of the image sensor 3 is much larger than the characteristic impedance of the drive signal line 7, it is possible to practically establish the impedance matching between the image sensor 3 and the drive signal line 7 by rendering a resistance of the terminal resistor 9 approximately equal to the characteristic impedance of the drive signal conductor 7.

Figure 4:
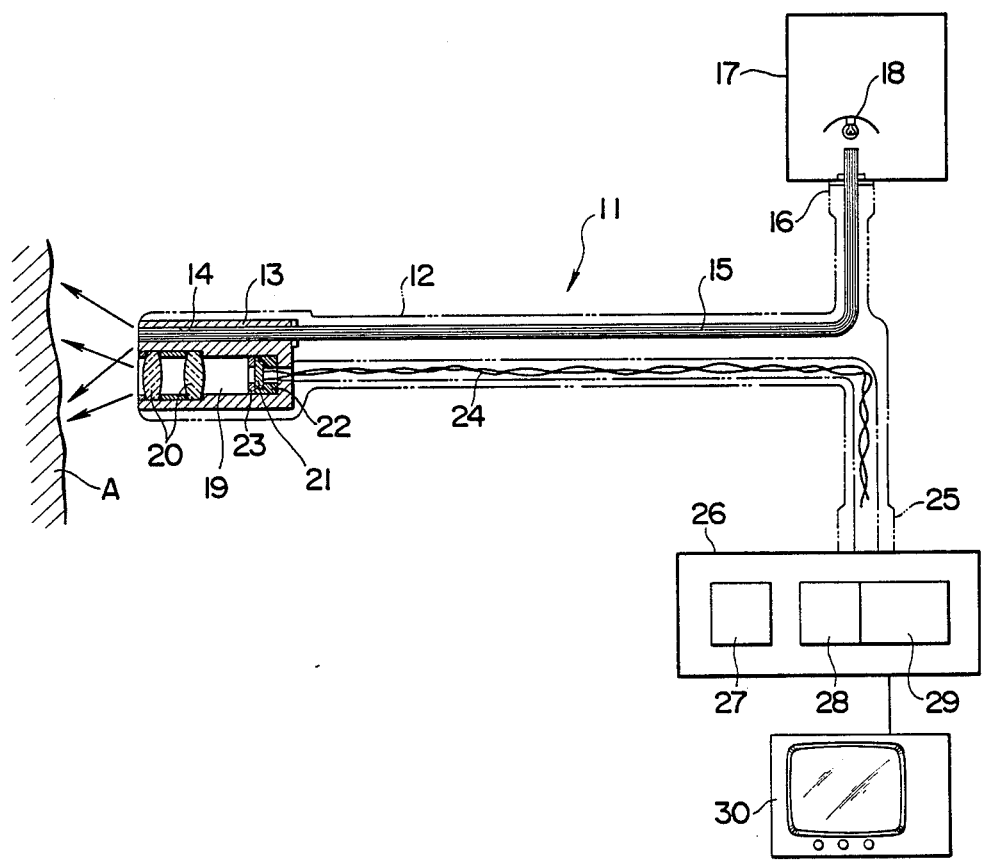
FIG. 4 is diagram illustrating a second embodiment of an electronic endoscope according to the present invention.
Figure 5:
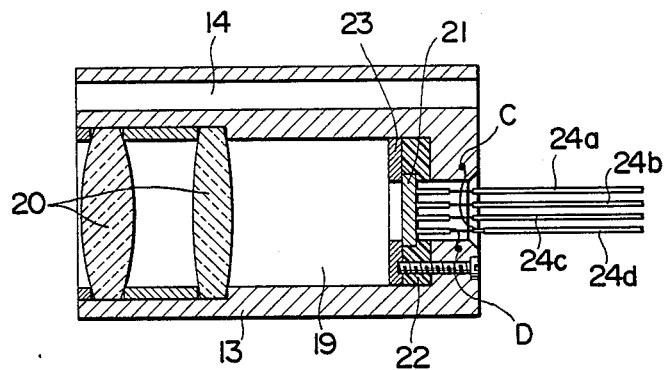
FIG. 5 is an enlarged sectional view of essential parts in the second embodiment.

In FIGS. 4 and 5, which show a second embodiment of the present invention, an electronic endoscope II has a distal for fixing front ends of internal members end structure at the distal end of an insertable portion 12 thereof and the proximal end of the insertable portion 12 is connected to an operation portion (not shown). The distal end structure has a frame body 13 for housing an image pickup system in which a fixing hole 14 is provided into which the front end of a light guide 15 for illumination composed of an optical fiber bundle is fixed. The light guide 15 is inserted into the insertable portion and light guide code of the endoscope 11 and the rear end of the light guide 15 is fixed to a connector 16. The connector 16 is connected to a light source 17 to face a lamp 18 within the light source 17. In addition, an opening 19 for image pickup is provided in the frame body 13 in parallel with the fixing hole 14 and an objective lens 20 is fixed in the front portion of the image pickup opening 19. A solid-state image sensor 21 is fixed between an insulating plate 22 and a ring-shaped retainer 23 at an image forming position of the objective lens 20. A signal line bundle 24 is connected to the image sensor 21 and to a power source unit 26 through the inside of the insertable portion 12 of the endoscope 11 by means of a connector 25. The power source unit 26 includes a power source 27 for supplying a power to the image sensor 21, a drive signal generator 28 for driving the image sensor 21 and an image signal processor 29 connected to a monitor television 30 for an image display.

The signal line bundle 24 comprises a grounding line 24a, a power supply line 24b, a signal output line 24c from the image sensor 21 and a drive signal line 24d. The signal output line 24c and drive signal line 24d are made of a coaxial cable or a shielding wire and their braided wires for shielding are connected to the grounding line 24a within the power source unit 26. The number of the drive signal lines 24d varies on types of the image sensor 21. For simplification, a single line 24d is shown. In the second embodiment, the frame body 13 constituting the distal end structure is utilized as the terminal resistor. The core of the drive signal line 24d is connected to a point D of the frame body 13 and the braided wire of the drive signal line 24d is connected to another point C of the frame body 13, such that the frame body 13 is constructed so as to give an impedance suitable for establishing the impedance matching between the two points C and D.

In operation, with the electronic endoscope 11 of the structure described above, illuminating light rays from the lamp 18 are emitted from an exit of the distal end structure through the light guide 15 to illuminate an area A to be inspected in a coelom. An image of the area A is formed through the objective lens 20 on an image pickup surface of the image sensor 21. On the other hand, an operating voltage from the power source 27 is supplied through the power line 24b and grounding line 24a to the image sensor 21 and a drive signal from the drive signal generator 28 is applied to the drive signal line 24d. An image signal formed on the image sensor 21 are successively read out and delivered through the signal output line 24c to the image signal processor 29 to be converted to a video signal such as an NTSC signal. The converted video signal is fed into the monitor television 30 to display the area A.

According to the second embodiment, since the frame body 13 of the distal end structure is employed as a terminal resistor so as to establish the impedance matching, it is possible to obtain a good image picture without causing distortion in waveform of a drive signal. In addition, assuming that a characteristic impedance of the drive signal line 24d is 50Ω, a resistance of the terminal resistor for the impedance matching is 50Ω, a waveform of the drive signal is a square wave of a duty ratio 50% and a voltage level is 10 Vpp, a consumption power of the terminal resistor is 1 W. When a resistor of 1 W is mounted on the distal end of an endoscope, the distal end structure of an endoscope practically increases in length and diameter. In the second embodiment, however, since the frame body 13 is utilized for the terminal resistor, it is possible to construct the distal end of an endoscope without making it larger.

While the above is described regarding reflection of the drive signal at the input terminal of an image sensor, the same is applicable to the output terminal of an image signal from the image sensor.

Similarly, in order to substantially equalize an output impedance of an output pin of the solid state image sensor to a characteristic impedance of the signal output line a matching resistor is added to the output side to establish the impedance matching, so that it is possible to prevent distortion in waveform due to signal reflection.

Figure 6:
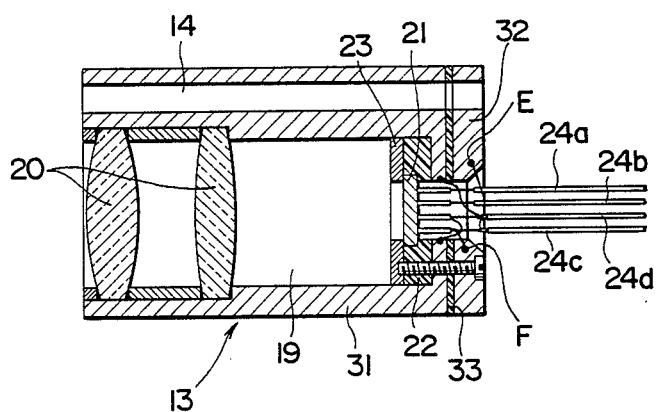
FIG. 6 is an enlarged sectional view of essential parts of a third embodiment of an electronic endoscope according to the present invention.

FIG. 6 shows a third embodiment of the present invention in which the impedance matching for an image signal is established. In the third embodiment, a frame body 13 of the distal end structure of an endoscope is divided into two parts, namely, a front frame body 31 in which an objective lens 20 and a solid-state image sensor 21 are fixed and a rear frame body 32 which is disposed so as to electrically separate with an insulating member 33 at the back of the front frame body 31. In addition, the core of a drive signal line 24d of the signal conductor bundle 24 is connected to a point of the front frame body 31 and the braided wire of the line 24d is connected to another point of the front frame body 31, thus rendering the front frame body 31 a terminal resistor for a drive signal, in a manner similar to the second embodiment. In addition, the core of a signal output line 24c is connected to a point F of the rear frame body 32 and the braided wire thereof is connected to another point E of the rear frame body 32, thus rendering the rear front body 32 a matching resistor for an output signal. The rear frame body 32 is so constructed as to be an impedance between two points EF suitable for establishing the impedance matching for the output signal line 24c.

According to the third embodiment, signal distortions in waveform can be prevented regarding an image signal as well as a drive signal and therefore a better image can be obtained.

In the foregoing embodiments, while the description is made with the separated power supply and light source apparatus, it may be applicable to those in a unity of them.

What is claimed is:

1. An electronic endoscope having a solid-state image sensor disposed at the distal end of the insertable portion thereof, characterized in that
    a terminal resistor for impedance matching is disposed within said distal end, and
    said terminal resistor is formed by a frame body of said distal end in which said solid-state image sensor is fixed.

2. An electronic endoscope according to claim 1 in which said frame body supports a lens for image pickup.

3. An electronic endoscope according to claim 2 in which said terminal resistor has a value such that an input and/or output impedance at the input and/or output terminal of said solid-state image sensor is nearly equal to an input and/or output characteristic impedance of an input signal line and/or a drive signal line of said image sensor.

4. An electronic endoscope according to claim 1 in which said terminal resistor has a value such that an input and/or output impedance at the input and/or output terminal of said solid-state image sensor is nearly equal to an input and/or output characteristic impedance of an input signal line and/or a drive signal line of said image sensor.

5. An electronic endoscope having a solid-state image sensor disposed at the distal end of the insertable portion thereof, characterized in that a terminal resistor for impedance matching is disposed within said distal end, said terminal resistor is connected to the input and/or output terminals of said solid-state image sensor in parallel therewith, said terminal resistor is formed by front and rear frame bodies which constitute a frame body of said distal end thereof and which are electrically separated into a plurality of parts on the input and output terminals of said solid-state image sensor.

6. An electronic endoscope according to claim 5 in which said terminal resistor has a value such that an input and/or output impedance at the input and/or output terminal of said solid-state image sensor is nearly equal to an input and/or output characteristic impedance of an input signal line and/or a drive signal line of said image sensor.

* * * * *